US009505003B2

(12) United States Patent
Sung et al.

(10) Patent No.: US 9,505,003 B2
(45) Date of Patent: Nov. 29, 2016

(54) PORTABLE REAL-TIME HEATING AND DETECTION DEVICE

(71) Applicant: Industrial Technology Research Institute, Hsin-Chu (TW)

(72) Inventors: Chih-Hsiang Sung, Keelung (TW); Tseng-Huang Liu, Kaohsiung (TW); Ruey-Shyan Hong, Taoyuan County (TW); Ting-Hsuan Chen, Taipei (TW); Ping-Jung Wu, Changhua County (TW); Kuo-Hsing Wen, Hsinchu County (TW); Wan-Chi Chang, New Taipei (TW)

(73) Assignee: INDUSTRIAL TECHNOLOGY RESEARCH INSTITUTE, Hsin-Chu (TW)

( * ) Notice: Subject to any disclaimer, the term of this patent is extended or adjusted under 35 U.S.C. 154(b) by 148 days.

(21) Appl. No.: 14/582,697

(22) Filed: Dec. 24, 2014

(65) Prior Publication Data

US 2016/0136647 A1 May 19, 2016

(30) Foreign Application Priority Data

Nov. 14, 2014 (TW) ............................ 103139622 A

(51) Int. Cl.
*B01L 7/00* (2006.01)
*C12M 1/38* (2006.01)
*B01L 9/06* (2006.01)

(52) U.S. Cl.
CPC .. *B01L 7/52* (2013.01); *B01L 9/06* (2013.01); *B01L 2200/18* (2013.01);
(Continued)

(58) Field of Classification Search
CPC .... B01L 7/52; B01L 99/00; B01L 2300/042; B01L 2300/0654; B01L 2300/1844; B01L 2300/1894
USPC .................................. 435/286.1, 287.2, 6.12
See application file for complete search history.

(56) References Cited

U.S. PATENT DOCUMENTS 6,586,233 B2 7/2003 Benett et al.
8,187,813 B2 5/2012 Chen et al.
(Continued)

FOREIGN PATENT DOCUMENTS

CN 101983236 A 3/2011
CN 103114032 5/2013
(Continued)

OTHER PUBLICATIONS

Taiwan Patent Office, Office Action, Oct. 15, 2015.
(Continued)

*Primary Examiner* — Michael Hobbs
(74) *Attorney, Agent, or Firm* — WPAT, PC; Justin King; Douglas A. Hosack

(57) ABSTRACT

A portable real-time heating and detection device includes a body, a cover and a detection unit. The body has an opening, and a base. The cover has a control unit and a fix unit. The detection unit is disposed on the base of the body and has a thermostat, an optical excitation, an optical detection, and a circuit board. The thermostat is disposed close to the opening and has at least one thermostat zone. The optical exciter is disposed between the thermostat and the base. The optical detector is disposed between the thermostat and the opening. The circuit board is electrical coupled to the control unit, the thermostat, the optical excitation, and the optical detector, respectively.

13 Claims, 5 Drawing Sheets

(52) U.S. Cl.
CPC . *B01L 2300/046* (2013.01); *B01L 2300/0663* (2013.01); *B01L 2300/1805* (2013.01); *B01L 2300/1844* (2013.01)

(56) References Cited

U.S. PATENT DOCUMENTS

| | | | |
|---|---|---|---|
| 2009/0275113 | A1 | 11/2009 | Maltezos et al. |
| 2011/0093207 | A1 | 4/2011 | Ingber et al. |
| 2012/0094373 | A1 | 4/2012 | Su et al. |

FOREIGN PATENT DOCUMENTS

| | | | |
|---|---|---|---|
| CN | 103173434 | | 6/2013 |
| EP | 2235196 | A2 | 10/2010 |
| TW | 201028470 | | 8/2010 |
| TW | 201332608 | | 8/2013 |
| TW | 201339308 | | 10/2013 |
| TW | M497667 | | 3/2015 |
| WO | 2012055073 | A1 | 5/2012 |

OTHER PUBLICATIONS

Wen Pin Chou, Ping Hei Chen, Jr Ming Miao, Long Sheng Kuo, Shiou Hwei Yeh, and Pei Jer Chen, "Rapid DNA amplification in a capillary tube by natural convection with a single isothermal heater" BioTechniques 2011 50:52-57.

R. Higuchi, C. Fockler, G. Dollinger and R., "Kinetic PCR analysis: Real-time monitoring of DNA amplification reactions" 9. Watson Bio/Technology 1993 11:1026.1030.

Madhavi Krishnan, Victor M. Ugaz, Mark A. Burns, "PCR in a Rayleigh-Benard Convection Cell" Science 2002 298 (25): 793.

Hsiao-Fen Grace Chang, Yun-Long Tsai,Chuan-Fu Tsai, Ching-Ko Lin, Pei-Yu Lee, Ping-Hua Teng, Chen Su and Chien-Chung Jeng, "A thermally baffled device for highly stabilized convective PCR" Biotechnology journal 2012 7 (5):662-666.

D. Braun, N. L.Goddard and A. Libchaber Phys. Rev. Lett."Exponential DNA replication by laminar convection" 2003 91: 158103.

Tsai YL, Lin YC, Chou PH, Teng PH, Lee PY J, "Detection of white spot syndrome virus by polymerase chain reaction performed under insulated isothermal conditions" Virol Methods. 2012 181(1):134-7.

E. K. Wheeler, W. Benett, P. Stratton, J. Richards, A. Chen, A. Christian, K. D. Ness, J. Ortega, L. G. Li,T. H. Weisgraber, K.Goodson, and F. Milanovich "Convectively Driven Polymerase Chain Reaction Thermal Cycler" Anal. Chem. 2004 76 (14): 4011-4016.

Yun-Long Tsai et al., "Development of TaqMan Probe-Based Insulated Isothermal PCR (iiPCR) for Sensitive and Specific On-Site Pathogen Detection" Sep. 2012.

PORTABLE REAL-TIME HEATING AND DETECTION DEVICE

CROSS REFERENCE TO RELATED APPLICATION

The present application is based on, and claims priority from, Taiwan (International) Application Serial Number 103139622, filed on Nov. 14, 2014, the disclosure of which is hereby incorporated by reference herein in its entirety.

TECHNICAL FIELD

The technical field relates to a portable real-time heating and detection device.

BACKGROUND

Polymerase chain reaction (PCR) is one of the popular nucleic acid amplification techniques in molecular diagnostics. Almost all commercial PCR systems adopt a thermocycler to perform heating and cooling and so as to have the deoxyribonucleic acid (DNA) to experience three typical temperature cycles; denaturation at 95° C., annealing at 45-65° C. and extension at 72° C. In each thermal cycle, a metal block is applied to transfer the heat to the reaction tube by thermal conduction, and a predetermined time is kept for reaction. However, such indirect heating method for PCR would spend lots of time in heating or cooling the metal block. Therefore, it is the reason why the reaction time of the PCR cycles is usually long and the systems for PCR always occupy too much space.

In addition, various developments on PCR chips with micro channels have been announced. In particular, the laboratory on a chip (LOC) is one of those devotions targeted to integrate micro channels and micro structures into the LOC capable of performing various reactions on a single chip, including various specimens' management, reactions, analysis or detections. Expectable advantages of the LOC are size miniaturization, rapid temperature control, reduction in the number of the required samples, cost-down and so on. However, though many researches demonstrate the merits of the PCR and LOC, yet a real mature commercial product of the PCR chip is yet to come. One of the reasons for such a situation in PCR chips is the low repeatability in the related researches. Furthermore, the requirement of a hydraulic driving system also limits the application of the PCR chips. Hence, it can be foreseen that the appearance of a commercial PCR chip shall need more efforts.

Currently, one of the temperature setting methods and structural designs for the PCR reactions is to place a test tube containing a mixture solution and DNA specimens into a sealed casing and then apply a heating device to heat the bottom portion of the test tube to the denaturation temperature so as to produce a temperature gradient thereof for further inducing a convection flow thereinside. Thereby, the PCR reaction can be maintained in a looping manner as the convection persists. In particular, the method and the apparatus for controlling temperature of the PCR are featured in simply structuring, low cost, requiring less time for changing temperatures, and being suitable to a single heat source environment.

Furthermore, a special reaction test tube furnished to a DNA amplification reaction includes mainly a plastic capillary tube wrapped with a metallic ring at the bottom. While this tube is arranged on a heating block with the metal ring contacting the block, the heat would be transferred to the liquid within the tube, such that the temperature of the liquid can be controlled around 95° C. In particular, the upper cap of the capillary tube is removable and thus can be applied by another temperature control at about 50° C., such that a temperature gradient between the bottom and the head of the tube can be controlled. Thereby, the PCR reagent inside the tube would be amplified time after time by the convective temperature cycling. Such a concept of heating the PCR reagent within the test tube which has a conductive ring under a single heat source is the topic of this current disclosure concerns.

SUMMARY

The present disclosure is to provide a portable real-time heating and detection device that can provide convenient portability to directly and promptly process an in-need PCR testing. The real-time detection results can be fed back to the touch panel interface so that the user can directly read the detection data in a real-time manner.

In one embodiment of the present disclosure, the portable real-time heating and detection device includes a body, a cover and a detection unit. The body further has an opening and a base. The cover further has a control unit and a fix unit, in which the fix unit is located above the opening of the body. The detection unit located on the base inside the body further has a thermostat, an optical exciter, an optical detector and a circuit board. The thermostat located at a side of the detection unit close to the opening further has at least one thermostat zone. The optical exciter is located between the thermostat and the base. The optical detector is located between the thermostat and the opening. The circuit board is electrically coupled respectively with the control unit, the thermostat, the heat-dissipation fan, the optical exciter and the optical detector. The control unit sends a temperature control command, a heat dissipation command, a stimulation command and a detection command through the circuit board, respectively, to the thermostat for performing corresponding temperature regulation upon the at least one thermostat zone, to the heat-dissipation fan for performing corresponding heat dissipation regulation upon the at least one thermostat zone, to the optical exciter for performing corresponding stimulation radiation upon the at least one thermostat zone, and to the optical detector for performing corresponding real-time stimulation light source detection upon the at least one thermostat zone. The optical detector sends a detected detection signal to the control unit via the circuit board so as to display a corresponding detection result in a real-time manner.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
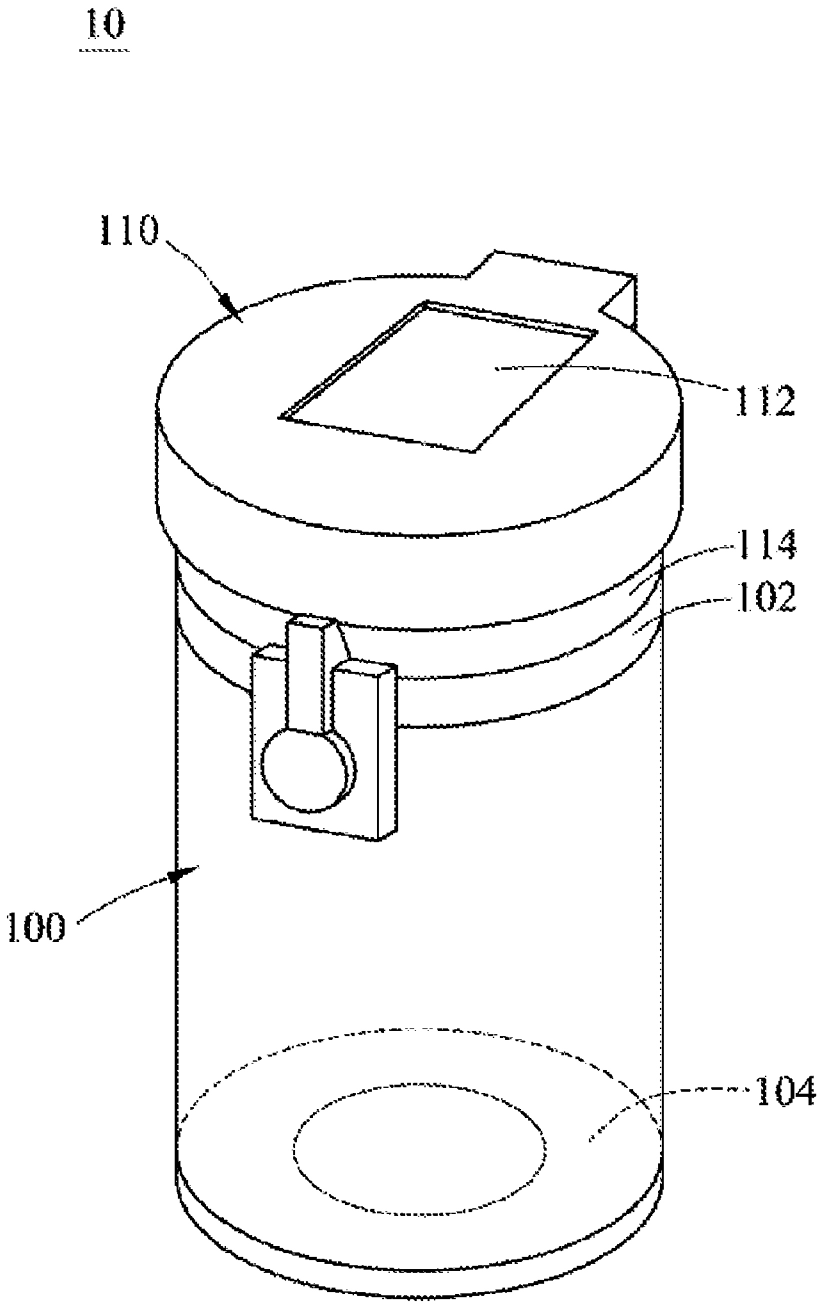
FIG. 1 is a perspective view of an embodiment of the portable real-time heating and detection device in this disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
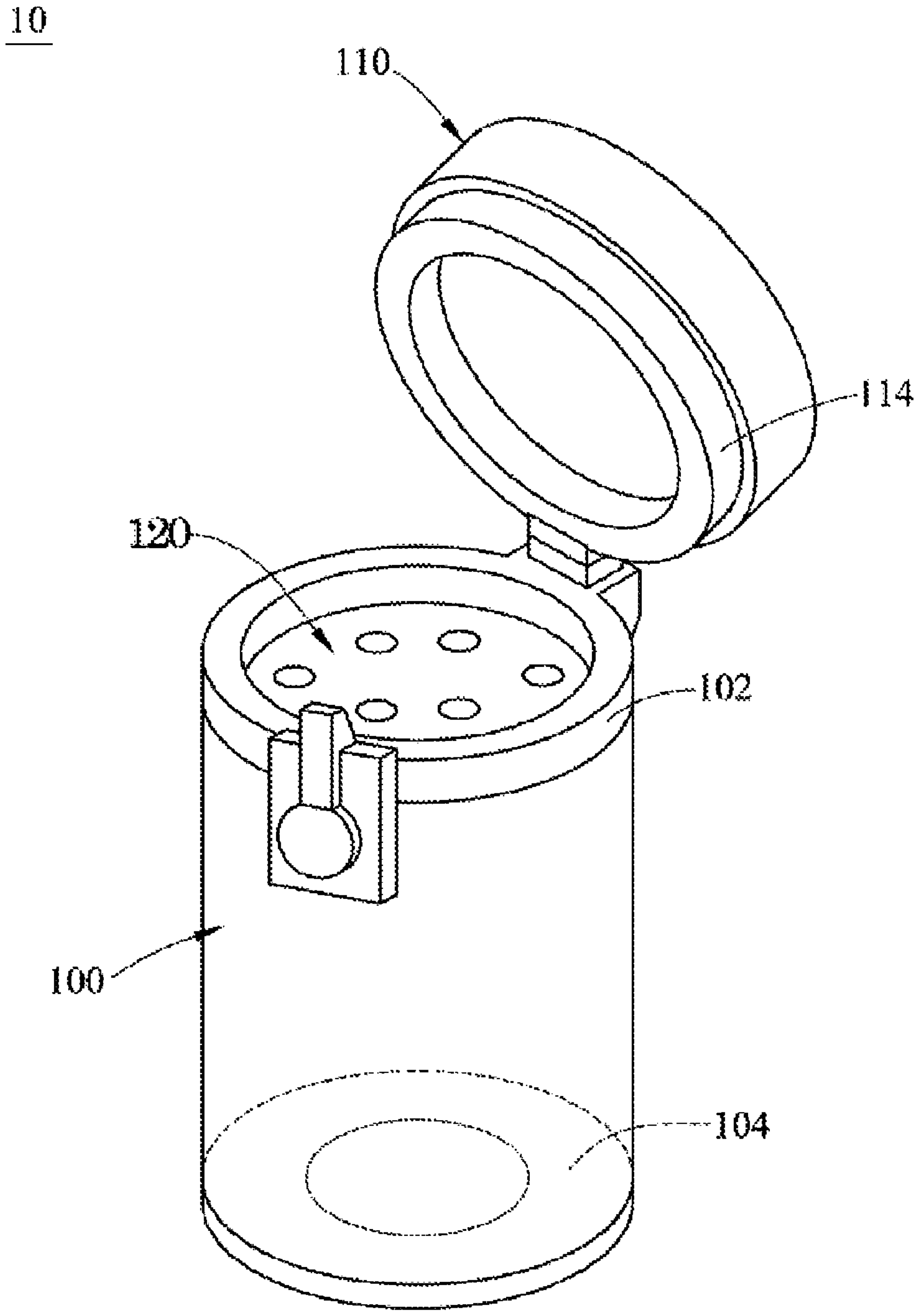
FIG. 2 is another view of FIG. 1 with the cover opened.
Figure 3:
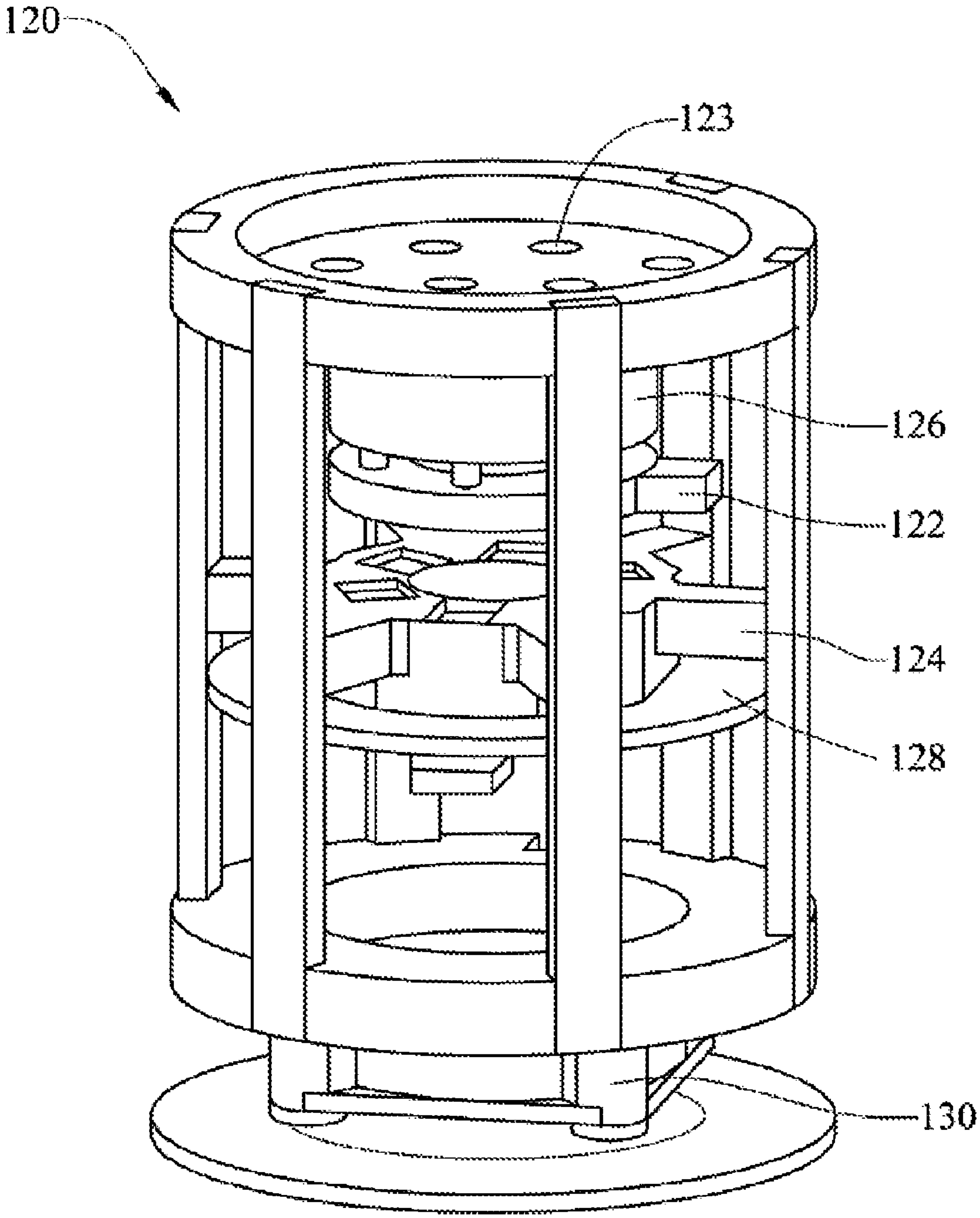
FIG. 3 demonstrates schematically an detection unit of the embodiment of FIG. 1.

Refer now to FIG. 1 to FIG. 3, in which FIG. 1 is a perspective view of an embodiment of the portable real-time heating and detection device in this disclosure, FIG. 2 is another view of FIG. 1 with the cover opened, and FIG. 3 demonstrates schematically a detection unit of the embodiment of FIG. 1. The portable real-time heating and detection device 10 includes a body 100, a cover 110 and a detection unit 120. The body 100 further has an opening 102 and a base 104. The cover 110 includes a control unit 112 and a fix unit 114. The fix unit 114 is located over the opening 102 of the body 100. In this embodiment, one end of the cover 110 is fixed above the opening 102 of the body 100 in a pivotal manner, so that the cover 110 can be pivoted to close or open the opening 102 of the body 100. In this disclosure, the control unit 112 can be a touch panel interface or a mechanical push button interface, and the fix unit 114 can be a plastic with a low thermal conductivity coefficient such as Bakelite® brand plastic. The detection unit 120 located on the base 104 inside the body 100 includes a thermostat 122, an optical exciter 124, an optical detector 126 and a circuit board 128. The thermostat 122 is disposed at a side thereof close to the opening 102 and further has at least one thermostat zone 123. In this disclosure, the thermostat 122 capable of heating and cooling can be a heating pad. The optical exciter 124 disposed between the thermostat 122 and the base 104 can have an LED as the light source thereof. The optical detector 126 located between the thermostat 122 and the opening 102 can be a photodiode, a charge coupled device (CCD) or a complementary metal-oxide semiconductor (CMOS). The circuit board 128 is electrically coupled respectively with the control unit 112, the thermostat 122, the optical exciter 124 and the optical detector 126.

In this disclosure, the control unit 112 can send a temperature control command, a heat dissipation command, a stimulation command and a detection command through the circuit board 128, respectively, to the thermostat 122 for performing corresponding temperature regulation upon the thermostat zones 123, to the heat-dissipation fan 130 for performing corresponding heat dissipation regulation upon the thermostat zones 123, to the optical exciter 124 for performing corresponding stimulation radiation upon the thermostat zones 123, and to the optical detector 126 for performing corresponding real-time stimulation light source detection upon the thermostat zones 123. The optical detector 126 sends a detected detection signal to the control unit 112 via the circuit board 128 so as to display a detection result in a real-time manner.

In this embodiment, the portable real-time heating and detection device 10 further includes a heat-dissipation fan 130 for performing heat dissipation upon the detection unit 120. In addition, elements for the body 100, the cover 110 and the detection unit 120 can be arranged in respective symmetric circling manners. Also, empty space shall be left in the symmetric centers of elements of the detection unit 120 and in the spacing between the elements of the detection unit 120 and the internal wall of the body. The base 104 also has a central hole for ventilation input from the heat-dissipation fan 130 located at one side of the base 104 and for flow circulation around the detection unit 120 so as to help to stabilize the overall detection temperature. The cover 110 can integrate the control unit 112 having the touch panel interface so as to allow the user to perform direct control for real-time reading the detection data.

Figure 4:
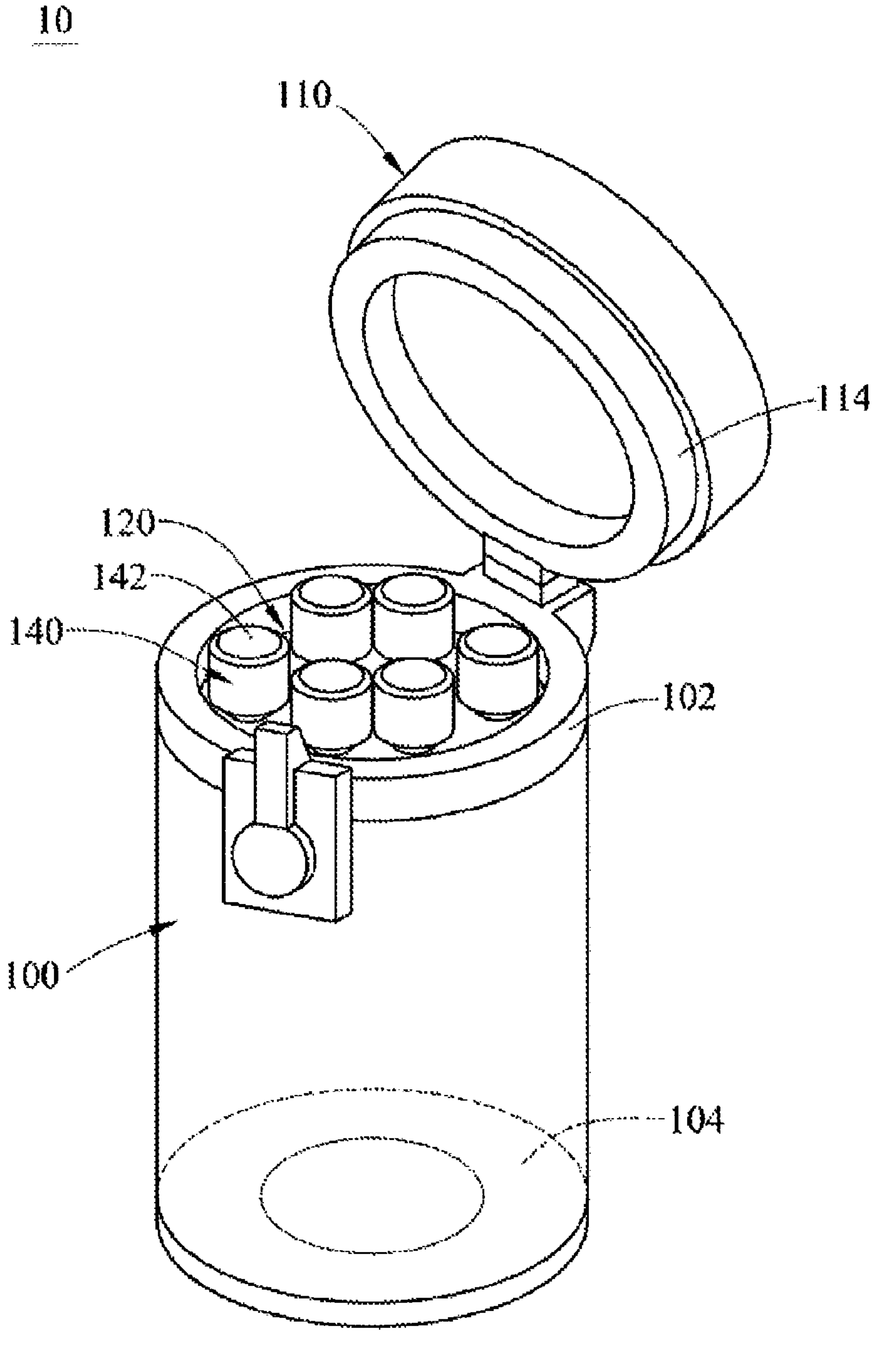
FIG. 4 is a view of an application of FIG. 2, in which a plurality of detection tubes is loaded.
Figure 5:
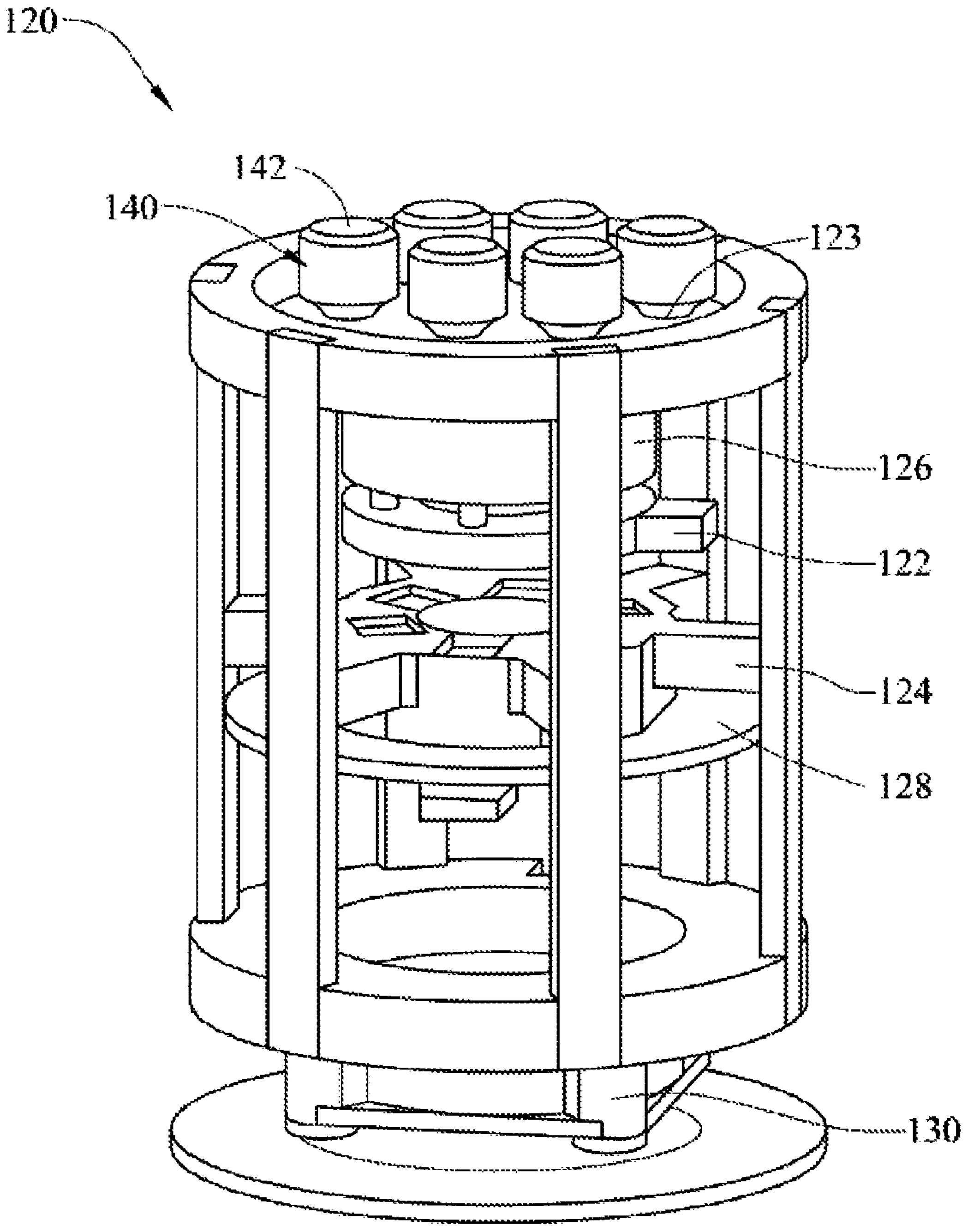
FIG. 5 is a view of an application of FIG. 3, in which a plurality of detection tubes is loaded.

Refer now to FIG. 4 and FIG. 5, in which FIG. 4 is a view of an application of FIG. 2, in which a plurality of detection tubes is loaded and FIG. 5 is a view of an application of FIG. 3 where a plurality of detection tubes is loaded. The portable real-time heating and detection device 10 further includes at least one detection tube 140 located above each of the thermostat zones 123 of the thermostat 122 for accommodating an object to be tested. The thermostat 122 can perform the temperature regulation upon each of the objects to be tested inside respective detection tubes 140 so as to generate corresponding heat convection inside the detection tubes 140. The optical exciter 124 can perform the stimulation radiation upon the objects to be tested. The optical detector 126 can detect the stimulation light sources of the stimulated objects to be tested and generate corresponding detection signals accordingly. When the fix unit 114 of the cover 110 is at a position to close the opening 102 of the body 100, the fix unit 114 would apply depression forcing upon each of the tube caps 142 of the corresponding detection tubes 140 so as to fix the tube caps 142 and thereby to serve an internal thermal conservation purpose for the portable real-time heating and detection device 10.

In summary, contrary to the conventional thermocycler, the portable real-time heating and detection device of this disclosure applies an adjustable temperature control to locally heat the detection tubes. By introducing the detection unit of this disclosure, a stable temperature gradient can be formed to each the object to be tested inside the detection tube. While in performing a PCR testing, the temperature regulation contributes a high temperature at the bottom of the detection tube for denaturation reaction. The temperature inside the detection tube would decrease gradually along an upward path there inside, and such a decrease in temperature (the temperature gradient) inside the detection tube would induce internal heat convection. The inside-tube heat convection flow would penetrate back and forth three different temperature zone piled inside the detection tube; i.e. denaturation at 95° C., extension at 72° C. and annealing at 45-65° C. Namely, if a DNA extension reagent is dissolved inside the detection tube where natural heat convection occurs, then the PCR reaction would be automatically completed after a substantial time of stay in the detection tube. Hence, the temperature control model of the portable real-time heating and detection device provided by this disclosure would be much simpler. Further, benefits from portability provided by the aforesaid portable real-time heating and detection device can contribute directly to the detection speed of an in-need PCR testing. By providing the detection device of this disclosure, real-time detection results would be able to be fed back to the touch panel interface anytime and anywhere for the user to directly access the detection data in a real-time manner.

It will be apparent to those skilled in the art that various modifications and variations can be made to the disclosed embodiments. It is intended that the specification and examples be considered as exemplary only, with a true scope of the disclosure being indicated by the following claims and their equivalents

What is claimed is:

1. A portable real-time heating and detection device, comprising:

a body, having an opening and a base;

a cover, comprising:

a control unit; and a depressor, mounted above the opening of the body; and a detection unit, located on the base inside the body, comprising:

a thermostat, located at a top side of the detection unit close to the opening, having at least one thermostat zone, wherein the thermostat zone is an area that interacts with a detection tube;

an optical exciter, located between the thermostat and the base;

an optical detector, located between the thermostat and the opening; and a circuit board, electrically coupled respectively with the control unit, the thermostat, the optical exciter and the optical detector;

wherein the control unit sends a temperature control command, a heat dissipation command, an excitation command and a detection command through the circuit board, respectively, to the thermostat for performing corresponding temperature regulation upon the at least one thermostat zone, to a heat-dissipation fan for performing corresponding heat dissipation regulation upon the at least one thermostat zone, to the optical exciter for performing corresponding excitation irradiation upon the at least one thermostat zone, and to the optical detector for performing corresponding real-time stimulated light detection upon the at least one thermostat zone, and the optical detector sends its detected signal to the control unit.

2. The portable real-time heating and detection device of claim 1, further including at least one detection tube located at respectively the at least one thermostat zone of the thermostat.

3. The portable real-time heating and detection device of claim 2, wherein the thermostat performs the temperature regulation upon an object to be tested inside one said corresponding detection tube so as to form an internal heat convection, the optical exciter perform the excitation irradiation upon the object to be tested, and the optical detector detects the signal of the stimulated light source produced by the object to be tested.

4. The portable real-time heating and detection device of claim 1, further including a heat-dissipation fan.

5. The portable real-time heating and detection device of claim 1, wherein the control unit is one of a touch panel interface and a mechanical push button interface.

6. The portable real-time heating and detection device of claim 1, wherein the depressor is Bakelite® brand plastic.

7. The portable real-time heating and detection device of claim 1, wherein the thermostat has both a heating function and a cooling function.

8. The portable real-time heating and detection device of claim 1, wherein the thermostat is a heating pad.

9. The portable real-time heating and detection device of claim 1, wherein a light source of the optical exciter is an LED.

10. The portable real-time heating and detection device of claim 1, wherein the optical detector is one of a photodiode, a charge coupled device (CCD) and a complementary metal-oxide semiconductor (CMOS).

11. The portable real-time heating and detection device of claim 1, wherein the depressor is made of a low thermal conductivity coefficient plastic.

12. The portable real-time heating and detection device of claim 1, wherein the control unit displays a corresponding detection result on a display in a real-time manner upon receipt of the detected signal from the optical detector.

13. The portable real-time heating and detection device of claim 1, wherein the control unit comprises a touch panel interface, and the control unit displays a corresponding detection result on said touch panel interface in a real-time manner upon receipt of the detected signal from the optical detector.

* * * * *